(12) United States Patent
Iordache et al.

(10) Patent No.: US 7,742,559 B2
(45) Date of Patent: Jun. 22, 2010

(54) MAMMOGRAPHY SYSTEM AND METHOD FOR ITS OPERATION

(75) Inventors: Razvan Gabriel Iordache, Paris (FR); Jose Abellan-Martinez, Buc (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/410,667

(22) Filed: Mar. 25, 2009

(65) Prior Publication Data
US 2009/0262887 A1    Oct. 22, 2009

(30) Foreign Application Priority Data
Apr. 17, 2008    (FR) .................................. 08 52595

(51) Int. Cl.
*A61B 6/04* (2006.01)
(52) U.S. Cl. ......................................... 378/37; 378/195
(58) Field of Classification Search ................... 378/37, 378/95, 98, 195, 196
See application file for complete search history.

(56) References Cited

U.S. PATENT DOCUMENTS

| | | | |
|---|---|---|---|
| 5,023,894 A | 6/1991 | Yamashita et al. | |
| 5,099,503 A | 3/1992 | Strommer | |
| 5,260,985 A * | 11/1993 | Mosby | ........................ 378/164 |
| 7,187,749 B2 | 3/2007 | Suzuki | |
| 2006/0067473 A1 | 3/2006 | Eberhard et al. | |
| 2007/0025503 A1 | 2/2007 | Hemmendorff | |
| 2007/0201617 A1* | 8/2007 | Nakayama et al. | ........... 378/108 |
| 2007/0211859 A1* | 9/2007 | Okada et al. | ................... 378/97 |
| 2008/0043904 A1 | 2/2008 | Hoernig | |
| 2008/0080668 A1* | 4/2008 | Kashiwagi | ..................... 378/37 |
| 2008/0181360 A1* | 7/2008 | Hemmendorff | ............... 378/37 |

OTHER PUBLICATIONS

"Development of Contrast Digital Mammography," Mia Skarpathiotakis, et al, American Association of Physicists in Medicine, Oct. 10, 2002 pp. 2419-2426.

* cited by examiner

*Primary Examiner*—Hoon Song
(74) *Attorney, Agent, or Firm*—Global Patent Operation

(57) ABSTRACT

A mammography system including a compression device, comprising two compression members to compress a breast, a sensor to sense the pressure exerted by the breast on one of the members and/or a device to determine the distance between the two members, an X-ray image acquisition system, means to adjust an initial position of the members. The system further comprises means to monitor variations in pressure and/or variations in thickness relative to their initial value, for an estimation of the risk of breast movement. The system further comprises means to present the user with information signaling breast movement, in relation to the estimation.

9 Claims, 4 Drawing Sheets

MAMMOGRAPHY SYSTEM AND METHOD FOR ITS OPERATION

CROSS-REFERENCE TO RELATED APPLICATIONS

This application claims priority under 35 U.S.C. §119(a)-(d) or (f) to prior-filed, co-pending French patent application serial number 0852595, filed on Apr. 17, 2008, which is hereby incorporated by reference in its entirety

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

The field of the invention relates to mammography.

2. Description of Related Art

In the area of application of an embodiment of the invention, one or more X-rays of a breast are taken, e.g. to investigate the breast tissue with a view to detecting the presence of tumours for example.

For this purpose, a device is used to compress the breast to be X-rayed between two compression members, so as to position the breast at the point provided for image acquisition and to obtain a substantially constant thickness of the breast between the two compression members over a certain width thereof, to achieve an image of the breast having substantially homogenous contrast over this width.

During a mammography examination requiring a series of images to be taken, the patient's breast remains between the compression members for ten seconds to a few minutes.

Said examinations using a series of images are described for example in the references given below: [1] concerning digital breast tomosynthesis (DBT), [2] concerning contrast-enhanced digital breast tomosynthesis and [3] concerning temporal contrast-enhanced digital mammography (Temporal CEDM).

In general, the objective of these methods is to take a limited number of breast X-ray images and, using adequate image processing systems, to reconstruct a three-dimensional, digital volume of the breast. The reconstructed three-dimensional volume consists of a plurality of reconstructed two-dimensional images called sectional planes, parallel to the plane of the X-ray detector and stacked along the axis perpendicular to the detector plane.

The compression exerted by the compression members on the breast does not, however, prevent the breast from moving as and when the successive X-ray images are taken.

Breast movements during image acquisition create artefacts and localization errors on the images, which may lead to deterioration of image quality and even make images unusable.

Frequently, several successive images of the breast are therefore taken at different angles using the same image acquisition apparatus.

If the acquisition time is short (a few seconds) the female patient can be requested not to breathe and not to move.

If the examination lasts longer, breathing and involuntary movements are difficult to prevent.

Movement of the breast, when an image is being taken, blurs the image. If the breast has moved between two images, there is no blur but shifting of the breast between the two images which may give rise to problems during post-processing of the images, thereby distorting the three-dimensional reconstruction of the breast.

Document U.S. Pat. No. 7,187,749 describes a blur compensation device for X-ray images, in which a sensor is moved by the movement of the object to be imaged, in this case a person's head. The sensor detects the change in position relative to a reference position on the basis of acceleration, angular speed or the angle of a supporting means for the object. Compensation means are provided to compensate for blur on a plurality of images, on the basis of movement calculated using the change in position, and the series of images thus compensated is then stored.

Document U.S. Pat. No. 5,099,503 describes a device to control the functioning of mammography equipment, in which the compression force applied by the breast holding means is measured. On the basis of this measurement, the speed of the compression movement is adjusted. When the breast is compressed by a compression plate, the speed of the compression motor is slowed when the compression force increases and, when the maximum allowable compression force has been reached, the compression motor is completely stopped to avoid excessive compression forces.

Document U.S. Pat. No. 5,023,894 relates to a device to correct data in a topographic image of a patient's head, in which head movement detection means, comprising a marker affixed to the head and a detector sensitive to the position of the marker or a camera, are provided to detect movements of the head. The head movement sensor is coupled to an address converting unit, which converts the data detected by the sensor into address correction data, in order to correct the tomographic image of the head.

Document US-A-2007/0025503 describes a method to acquire mammographic images which provides for image data acquisition by an X-ray system and automatic analysis of the acquired images by said system, analysing blur due to movement, and indicates whether there is blur due to movement.

These known prior art systems have several drawbacks.

The compensation or correction of an image by calculation, in the event of breast movement, is cumbersome and complicated to apply. In practice it is difficult to implement automatic image or image data analysis that is satisfactory. Additionally, image correction is most often oversized compared with the actual needs of a mammography technician.

A marker placed on the breast is not recommended for the following reasons:

the marker will inevitably lie in the field of the images and may affect the images taken if it is radioopaque, the positioning of the marker must be fairly precise and constant irrespective of breast morphology, so that it remains within the detection limits of movement, the movement system must be initialized so that it records the initial position of the marker after breast compression, the examination is already sufficiently traumatizing and painful for the patient without adding any additional steps to the imaging protocol.

Finally, control over the speed of the motor moving the breast compression plate is sufficient to achieve proper breast compression before taking any images, but does not prevent the breast from moving once the motor is stopped and the compression plate has been immobilized.

BRIEF SUMMARY OF THE INVENTION

The invention sets out to obtain a mammography system which solves the problem due to breast movements and overcomes the drawbacks of the prior art.

For this purpose, one first subject-matter of an embodiment of the invention is a mammography system that comprises a compression device comprising at least two compression members to compress a breast arranged therebetween. The system further comprises at least one sensor to sense the pressure exerted by the breast on at least one of the compression members, and/or a device to determine the distance between the two compression members, representing the thickness of the breast compressed between the members. The system further comprises a system to acquire X-ray images of the breast arranged between the compression members. The system further comprises means to adjust an initial position of the compression members, in which the pressure and/or the thickness has an initial value. The means to adjust an initial position may further comprise means to monitor variations in pressure and/or variations in thickness relative to their initial value, for an estimation of the risk of breast movement in relation to said variations, and means to present information comprising a user interface and providing the user with information signalling movement of the breast in relation to said estimation.

According to other characteristics of the invention:

The monitoring means are provided to trigger the sending of information signalling breast movement when the variation in pressure and/or variation in thickness relative to their initial value exceeds a prescribed threshold above or below the initial value.

The means to present information signalling breast movement comprise means to add this information signalling breast movement to at least one X-ray image acquired by the acquisition system for the time corresponding to the estimated duration or the estimated time of breast movement.

The X-ray image acquisition system comprises means to present X-ray images, the means to present information being separate from the means to present X-ray images.

The system comprises means to record estimations of risk of movement made by the monitoring means in association with time identification, allowing determination of the instant of time or time interval at or during which the corresponding variation occurred.

The mammography system is provided with said at least one sensor to sense the pressure exerted by the breast on at least one of the compression members, said compression members comprise an upper compression member mobile with respect to a lower fixed compression member, the pressure sensor is provided on the upper mobile compression member.

The monitoring means, the information presenting means, the user interface are provided in a removable module able to cooperate with a base of the system to ensure their functions.

The mammography system is provided with said at least one sensor to sense the pressure exerted by the breast on at least one of the compression members, the receiver base of the removable module is located on the compression member which carries said pressure sensor.

A second subject of an embodiment of the invention is a method to operate a mammography system such as described above provided with said at least one sensor to sense the pressure exerted by the breast on at least one of the compression members, wherein:

the compression members are moved relative to each other so as to compress the breast arranged therebetween, until an initial pressure value is reached, the movement of the compression members is stopped when the pressure reaches the initial pressure in the initial position, after the compression members have been stopped in the initial position, the pressure exerted by the breast on one of the compression members and/or the thickness of the breast compressed between the compression members is/are measured, the variations in pressure and/or variations in thickness are monitored relative to their initial value to estimate breast movement in relation to said variations, and the sending of information to the user signalling breast movement is triggered, in relation to the estimated risk of movement, this information being sent to an interface.

BRIEF DESCRIPTION OF THE DRAWINGS

Embodiments of the invention will be better understood on reading the following description given solely as non-limiting examples with reference to the appended drawings in which.

DETAILED DESCRIPTION OF THE INVENTION

Figure 1:
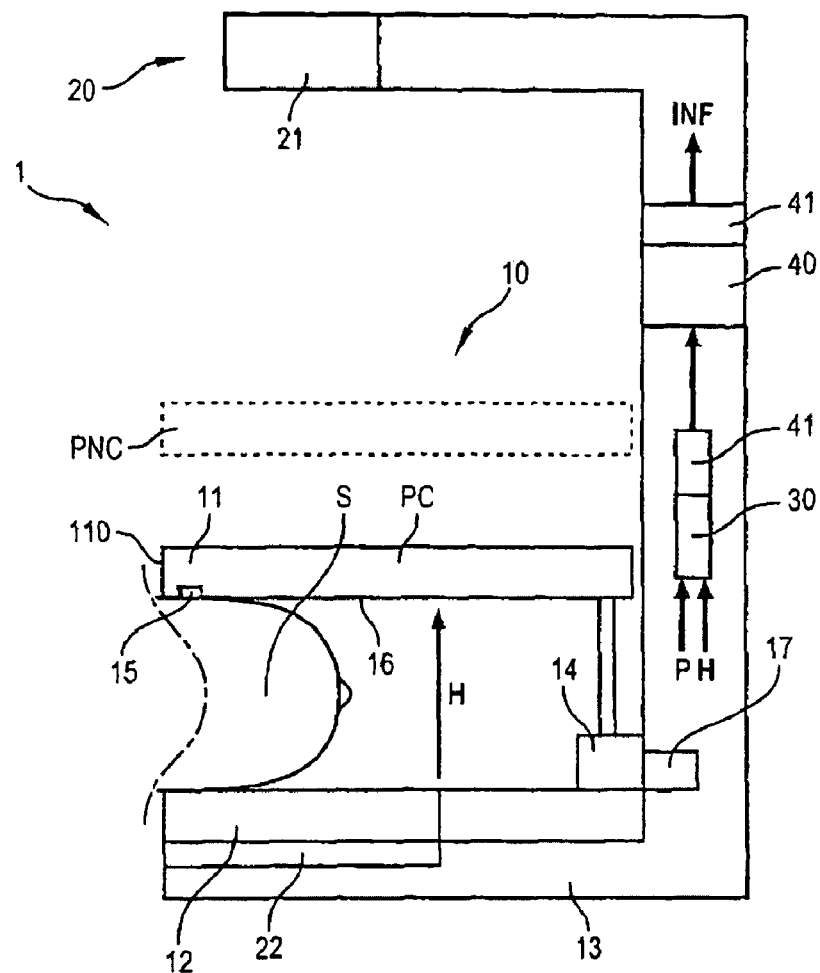
FIG. 1 is a schematic view of a mammography system according to an embodiment of the invention.

In FIG. 1, the mammography system 1 comprises a breast compression device 10, comprising a first compression member 11 and a second compression member 12. For example, in the case shown in FIG. 1, the compression member 12 acts as support means for the breast S and is therefore a lower member, whilst member 11 is the upper member located above the breast.

The system 1 comprises a system 20 to acquire X-ray images of the breast, comprising firstly an X-ray source 21 and secondly a plate or any other means 22 to record an X-ray image of the breast S, the image recording means 22 being located on the other side of the breast S relative to the source 21.

The first member 11 lies away from the second member 12 in a direction H. The first member 11 and the second member 12 are mobile relative to one another. For example, member 11 is mobile relative to member 12 attached to a fixed frame 13 of the system 1, carrying the source 21. The source 21 is provided for example on the upper part of the frame 13 above the upper member 11. The mobile member 11 is called the compression paddle for example. Members 11 and 12 are each formed of a planar plate for example, as is known. The members 11 and 12 could evidently assume a position other than upper and lower to compress the breast S.

Figure 6:
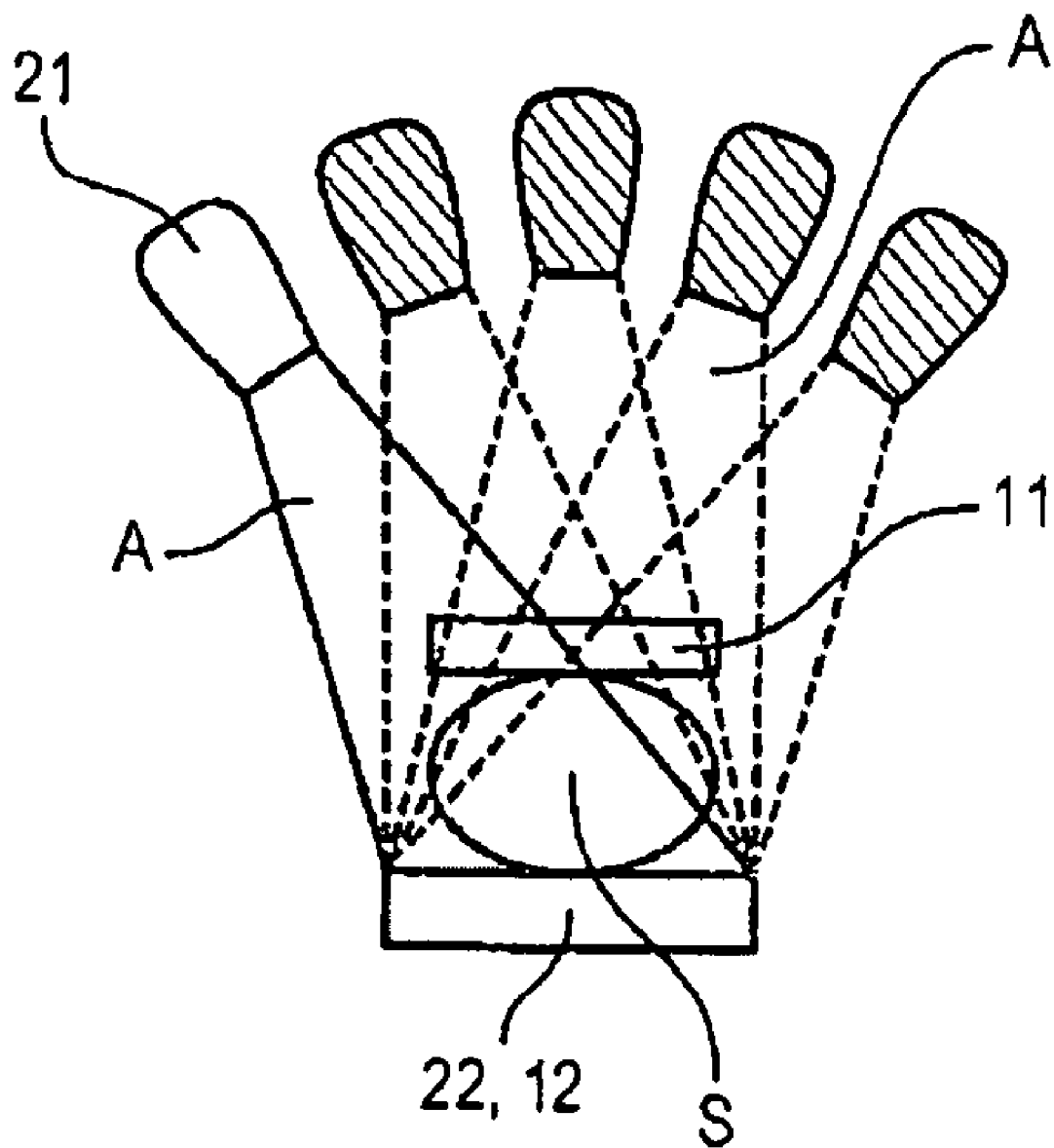
FIG. 6 is a diagram showing the different angles at which images are taken during a mammography examination using the system according to FIG. 1.

In general, the detector 22 and the lower member 12 are fixed relative to the frame, and the X-ray source 21 is mobile so that it is able to take images at different angles A, as is shown FIG. 6.

The breast compression device 10 comprises means 14 to move the two members 11 and 12 with respect to each other, to cause them to draw together in direction H so as to compress the breast S arranged between the members 11, 12 and to adjust the position taken up by members 11, 12 relative to each other. The means 14 to move members 11, 12 relative to each other comprises a motorized mechanism for example, as is known.

In a first unoccupied position PNC shown as a dashed line in FIG. 1, member 11 is sufficiently distanced away from member 12 to allow insertion of the breast S between the members so that it is not compressed.

Then, during an initial step E2 of compression of the breast S, member 11 is drawn towards member 12 by commanding means 14 to reduce the inter-distance H so as to compress the breast S gradually as far as an initial position PC shown as a solid line in FIG. 1.

In this initial position PC, the breast S has a constant thickness between the members 11 and 12 at its rear part, i.e. not at its front edge shown on the right in FIG. 1. When an X-ray of the breast S is taken compressed in this manner, the X-rays are directed through this thickness between the members 11, 12. Therefore the distance H between the members 11, 12 is called the radiological thickness of the compressed breast S.

One of the compression members, e.g. the mobile member 11, comprises a pressure sensor 15 on its surface 16 facing the breast S. The sensor 15 is arranged so that it contacts the breast S when it is compressed between the members 11, 12. The sensor 15 therefore provides a measurement of the pressure exerted by the breast S on the member 11 carrying the sensor. The sensor 15 is for example located close to the end 110 of member 11 facing the patient's body, i.e. the end delimiting the side of insertion of the breast S between the members 11, 12 on device 10.

Means 17 are also provided on the system, to measure or calculate the distance H between the compression members, representing the thickness of the breast S.

Figure 4:
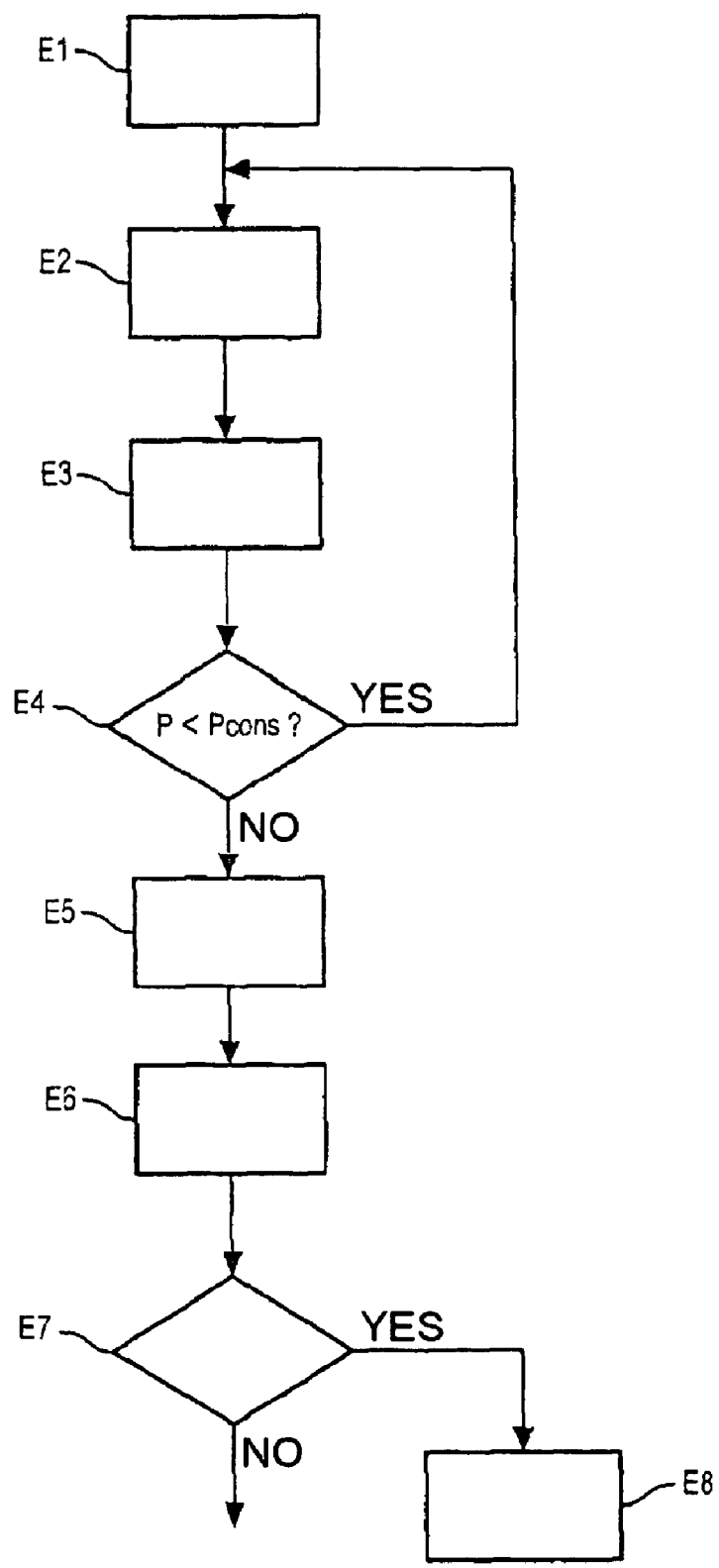
FIG. 4 is a flow chart of a method to operate the mammography system according to an embodiment of the invention.

In FIG. 4, an initial value Pcons for the pressure P of the breast S is fixed during a step E1.

Then the breast S is compressed by drawing members 11, 12 towards each other, at a step E2.

Next, during step E3, the pressure P of the breast S is determined by the sensor 15 and the thickness H of the breast is determined using means 17.

At step E4, a calculation unit 30 determines whether pressure P is lower than the initial pressure Pcons. In the affirmative, a return is made to step E2 to increase breast compression by reducing thickness H. If not, the procedure moves on to step E5.

At step E5, the movement of members 11, 12 relative to one another is stopped, and they are fixed at the initial position PC. Pressure P is then substantially equal to the initial pressure Pcons, and the thickness H is set at an initial value Hcons. This initial position PC is the intended position to take X-ray images, by system 20, of the breast S compressed between the members 11, 12.

After step E5, in which the compression members 11, 12 are stopped, the calculation unit 30 of system 1, via suitable means, monitors at step E6 whether the pressure P of the breast determined by the sensor 15 and/or the thickness H of the breast undergo any variations in value over time.

Figure 3:
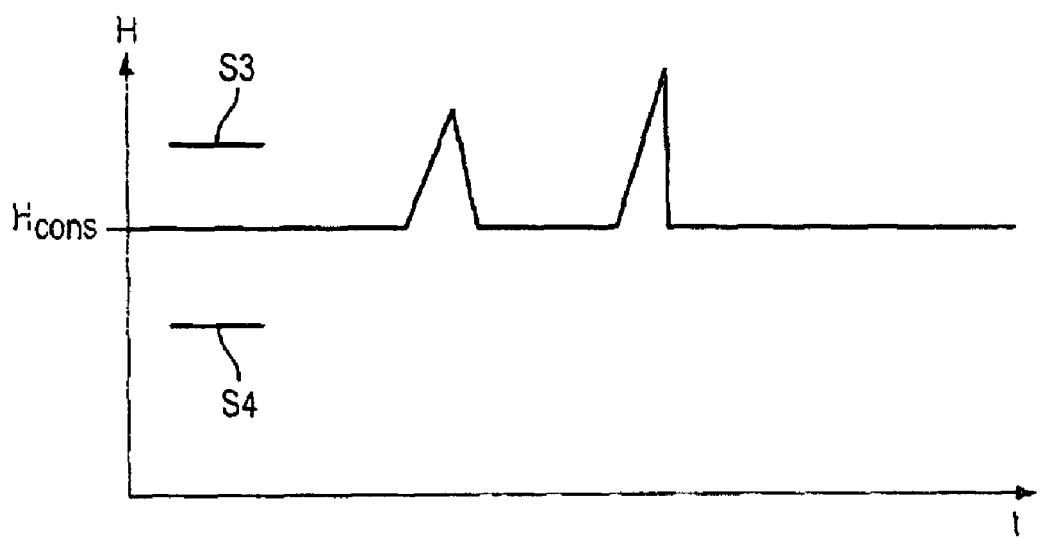
FIG. 3 is a diagram of a second magnitude detected on the mammography system, in relation to time.
Figure 2:
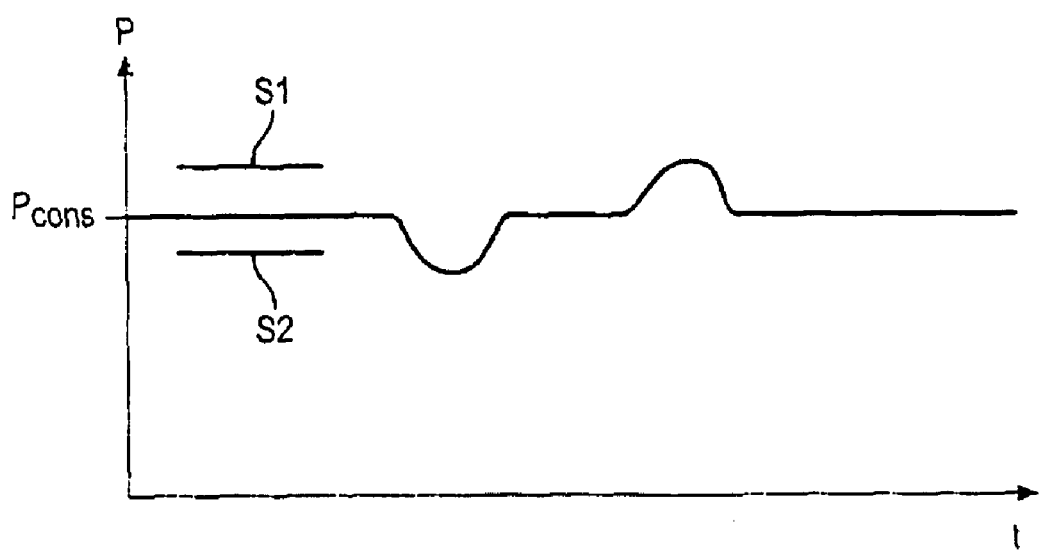
FIG. 2 is a diagram showing changes of a first magnitude detected on the mammography system, in relation to time.

FIGS. 2 and 3 give examples of said possible variations. In FIGS. 2 and 3, the thickness H or the pressure P are servo-controlled by a set point, and therefore their variation is in the form of a peak or bump. If the values are not servo-controlled, their variation would be in stepped form. In both cases, variation is detectable and allows embodiments of the invention to be implemented.

Since the breast is held compressed between the members 11, 12 in their initial position PC, any breast movement creates peaks for example in the graph plotting thickness H against time, above the initial constant thickness Hcons symbolized by the constant value plateau, as is shown FIG. 3. If there is no movement of the breast from the initial position PC, there are no such peaks and the graph is plotted in the form of the plateau Hcons of constant value.

Similarly in FIG. 2 any movements of the breast, compressed between members 11, 12 in the initial position PC, create hollows or bumps in the pressure graph P of the breast respectively below or above the initial constant value Pcons, symbolized by the constant value plateau. If there is no breast movement in the initial position PC, the graph of pressure P is equal to the plateau Pcons of constant value, with no variation around this value.

The calculation unit 30 comprises monitoring means which, using these variations in pressure P and/or thickness H relative to their initial value Pcons, Hcons, provide an estimation of the risk of breast movement during step E7. This estimation of the risk of breast movement is calculated in relation to variations in P and/or H, and for example solely in relation to the pressure P of the breast. The variation in pressure P and/or thickness H relative to their initial value Pcons, Hcons represents the amplitude of any momentary movement of the breast.

After step E5 in which compression members 11, 12 are stopped, step E6 to monitor actual pressure P and/or actual height H is conducted for as long as the breast S is held compressed between the members 11, 12, in the initial position PC.

Monitoring step E6 is followed by step E7 to estimate risk of movement.

During step E7 to estimate risk of movement, the calculation unit 30 determines whether or not the mammography technician must be warned that the breast has just moved or of a risk that the breast may have moved. The system comprises means 40 to present information which may be visual and/or sound means such as a display screen, speaker, or other, to provide the mammography technician with information signalling movement of the breast.

For example, at step E7, it is examined whether the variation in the monitored actual pressure P of the breast exceeds a first prescribed threshold S1 above the initial pressure Pcons and/or falls to below a second prescribed pressure threshold S2 below the initial pressure Pcons, and/or whether the actual monitored thickness H of the breast exceeds a third prescribed threshold S3 above the initial thickness Hcons and/or falls below a fourth prescribed threshold S4 below the initial thickness Hcons.

If one these thresholds S1, S2, S3, S4 is exceeded as indicated, or if the calculation unit 30 estimates that the movement represented by the variation in the monitored value of P and/or H is too high (i.e. if the finding is YES after monitoring step E7), the calculation unit 30 triggers the sending of a signal INF indicating breast movement to the information presenting unit 40 which then reproduces this information INF on an interface 41 so that it can be seen or heard by the mammography technician during step E8. The interface 41 may be visual and/or sound and may for example include a speaker, a warning light or any other signalling means. For example the interface 41 is separate from the interface used to show X-ray images of the breast on system 20, which usually comprises an image display screen.

The X-ray images of the breast are taken by the acquisition system 20 after step E5 and, when applicable, between or during steps E6, E7, E8. Estimations of risk of movement made by the calculation unit 30 at step E7 in relation to variations in the actual monitored value P and/or H, are recorded for example against time in a memory 32 or any other recording means 32. In this case, as a variant or in addition to the above example, the information INF on breast movement can be delivered to the user by being added to the acquired image or images whose acquisition time corresponds to the instant or time interval during which the variation in the monitored value P or H occurred. The information INF signalling breast movement is separate from the X-ray images of the breast and their image data. The information INF signalling breast movement is present for example on the image display screen or on the actual X-rays themselves. The mammography technician will therefore know that an image carrying this movement information INF was taken while the breast moved, and this information can be used for example to discard this image. On the contrary, in this embodiment, if an image does not carry said information INF signalling movement, the mammography technician will be reassured that the image was taken under sufficiently good conditions of breast immobility and that the image can therefore be kept and validated for analysis.

In another embodiment, the estimation of risk of movement is calculated using standard deviation from the actual monitored value P and/or H relative to its initial value Pcons, Hcons. Information INF signalling movement will then be a quantification of the risk of movement for example, in which the risk of movement is evaluated as being greater, the greater the standard deviation.

Figure 5:
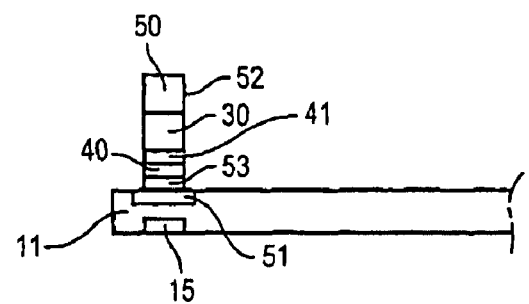
FIG. 5 is diagram of an alternative embodiment of the system according to the invention.

In the embodiment shown FIG. 5, the monitoring means, presentation means 40 and the interface 41 are located on a removable module 50 contained in a casing 52. The module 50 cooperates in mounting position with a fixed base 51 of system 1, provided for example on the compression member 11 carrying the pressure sensor 15. The module 50 comprises connecting means 53 with the base 51 allowing the mounting and dismounting of the module 50 on the base 51. These connecting means 53 may be contacting means with the base 51, or may also have wireless connection with the base 51.

A first application mode of the invention is an instant mode. A second application mode of the invention is an a posteriori mode.

In the first mode with real-time estimation of the risk of movement:
there is a great risk of instant movement, if one or a sub-set of monitored parameters shows an instant variation that is greater than a predefined threshold of instant variation,
there is a great risk that the breast will move during current acquisition if one or a sub-set of monitored parameters shows a significant change (more than a predefined threshold of intra-acquisition variation) during one of the image acquisitions in the sequence,
there is a great risk that the breast has moved between current acquisition and a preceding acquisition if one or a subset of monitored parameters changes significantly (more than a predefined threshold of intra-acquisition variation) between the current image and a preceding image in the sequence.

In the first mode, to inform the technician of risk estimations, when a great risk of movement has been detected the acquisition is stopped and/or the X-ray technician is warned (sound and/or visual warning on the acquisition monitor).

In the second mode with a posteriori estimation of risk of movement, the following parameters are calculated and displayed to assist the X-ray technician in controlling the quality of acquisition for example:
global risk of movement: what is the risk that the breast has moved during acquisition? This risk can be proportional to the standard deviation from one, all or a subset of monitored parameters,
risk of movement between acquisition i and j (particular case between i and i+1): can, for example, be proportional to the difference between the mean values of one, all or a subset of monitored parameters during acquisition i and j respectively,
risk of movement during acquisition i: for example proportional to the maximum difference between the values of one, all or a subset of monitored parameters during acquisition i.

To feed a posteriori estimations of risk back to the technician, the risk levels are displayed for the X-ray technician when examining the sequence of acquired images (or sectional images reconstructed for digital breast tomosynthesis—DBT). For example, the images carrying great risk of movement may flash for a few seconds when displayed. Sound may also be used.

The above-mentioned parameter thresholds may be determined by calibration for example. This can be done using an anthropomorphic model (phantom) of a breast having radio-opaqueness substantially equivalent to a breast. The anthropomorphic phantoms are compressed and they are caused to move during the acquisition sequence. The parameters are monitored and the threshold is chosen at which movement is not acceptable. Movement can be monitored by movement sensors on the phantom, or by evaluation of the image quality of known structures of interest in the phantoms—after DBT reconstruction, or after Temporal CEDM subtraction for example.

It is also possible to provide for filtering of the patient's physiological movements (e.g. breathing, a periodic movement of around 5 seconds) and elastic release of the breast subjected to compression (continuous variation over a very slight slope). According to one improvement, provision is made to eliminate breathing movements and changes in breast thickness, caused by the application of a constant force. This can be performed before real-time and/or a posteriori estimation of risk.

For breathing movement, as it is periodical, this can be estimated by determining the maxima of self-correlation functions for monitored parameters, and can be eliminated by filtering using a notch filter.

Reaction to force is constant relaxation of breast tissues, leading to a constant decrease in breast thickness (under constant pressure). For example the linear slope can be eliminated from the signals before estimation of risk.

In the prior art, during a first step the breast is compressed (to obtain a pre-adjusted pressure force on the breast for example) and during a second step, during the full compression period, at least one parameter is maintained constant: compression thickness or the pressure applied to the breast or the compression device is locked in the position obtained at step 1.

According to an embodiment of the invention, the risk of movement during compression is monitored. During the full compression period at least one of the parameters: compression thickness, pressure applied to the breast, force/deformation of the compression paddle, is monitored. The control parameter may be one of those cited above.

According to an embodiment of the invention, provision is made for the mammography system to comprise:

means (30) to monitor variations in pressure and/or variations in thickness relative to their initial value (Pcons, Hcons), to calculate an estimation of risk of breast movement in relation to any variations, means to estimate a level of breast movement risk, whose input is the information on variations in monitored values and whose output is an estimated value for risk of breast movement, and means to present information comprising a user interface (41) to provide the user with information (INF) signalling breast movement in relation to said estimation.

LIST OF REFERENCES

[1] DBT (digital breast tomosynthesis)—Niklason L T, Christian B T, Niklason L E, et al: Digital tomosynthesis in breast imaging. Radiology 205:399-406, 1997.

[2] CE-DBT (contrast-enhanced DBT)—Puong, Sylvie; Patoureaux, Fanny; Iordache, Razvan; Bouchevreau, Xavier; Muller, Serge. Dual-energy contrast enhanced digital breast tomosynthesis: concept, method and evaluation on phantoms. Medical Imaging 2007: Physics of Medical Imaging. Proceedings of the SPIE, Volume 6510, pp. 65100U (2007).

[3] Temporal CEDM (contrast-enhanced digital mammography)—Skarpathiotakis M, Yaffe M J, Bloomquist A K, Rico D, Muller, S Rick. A Development of Contrast Digital Mammography. Medical Physics 29 (10) 2419-2426, 2002.

What is claimed is:

1. A mammography system, comprising:
a compression device comprising at least two compression members to compress a breast arranged therebetween;
at least one sensor to sense the pressure exerted by the breast on at least one of the compression members, and/or a device to determine the distance between the two compression members, representing the thickness of the breast compressed between the members;
a system to acquire X-ray images of the breast arranged between the compression members;
means for adjusting an initial position of the compression members, in which the pressure and/or the thickness has an initial value;
wherein the means to adjust an initial position comprises:
means for monitoring variations in pressure and/or variations in thickness relative to their initial value, for an estimation of the risk of breast movement in relation to said variations,
means for presenting information comprising a user interface and providing the user with information signalling movement of the breast in relation to said estimation.

2. The mammography system of claim 1, wherein the monitoring means are configured to trigger the sending of information signalling breast movement when the variation in pressure and/or variation in thickness relative to their initial value exceeds a prescribed threshold above or below the initial value.

3. The mammography system of claim 1, wherein the means for presenting information signalling breast movement comprise means for adding this information signalling breast movement to at least one X-ray image acquired by the acquisition system for a time corresponding to the estimated duration or an estimated time of breast movement.

4. The mammography system of claim 1, wherein the X-ray image acquisition system further comprises:
means for presenting X-ray images, the means for presenting information being separate from the means for presenting X-ray images.

5. The mammography system of claim 1, further comprising:
means for recording estimations of risk of movement made by the monitoring means in association with time identification to allow determination of an instant of time or time interval at or during which the corresponding variation occurred.

6. The mammography system of claim 1, wherein said compression members comprise an upper compression member mobile with respect to a lower fixed compression member, and
wherein the pressure sensor is provided on the upper mobile compression member.

7. The mammography system of claim 1, wherein the monitoring means, the information presenting means, and the user interface are provided in a removable module configured to cooperate with a base of the system.

8. The mammography system of claim 7, wherein a receiver base of the removable module is located on the compression member that carries said pressure sensor.

9. A method of operating a mammography system having at least one sensor to sense the pressure exerted by a breast on at least one of a plurality of compression members, the method comprising:
moving the compression members relative to each other to compress the breast arranged therebetween, until an initial pressure value is reached;
stopping the movement of the compression members when the pressure reaches the initial pressure;
measuring, after the compression members have been stopped in an initial position, a pressure exerted by the breast on one of the compression members and/or measuring a thickness of the breast compressed between the compression members;
monitoring variations in pressure and/or variations in thickness relative to their initial value to estimate breast movement in relation to said variations; and
triggering sending of information signalling breast movement, in relation to the estimated risk of movement, to an interface.

* * * * *